United States Patent [19]

Klose et al.

[11] Patent Number: 4,515,889

[45] Date of Patent: May 7, 1985

[54] METHOD FOR CARRYING OUT ANALYTICAL DETERMINATIONS

[75] Inventors: Sigmar Klose, Berg; Fritz Stähler, Tutzing; Hans Lange, Lampertheim; Wolfgang Kleemann, Tutzing, all of Fed. Rep. of Germany

[73] Assignee: Boehringer Mannheim GmbH, Mannheim-Waldhof, Fed. Rep. of Germany

[21] Appl. No.: 323,205

[22] Filed: Nov. 20, 1981

[30] Foreign Application Priority Data

Nov. 25, 1980 [DE] Fed. Rep. of Germany ....... 3044385

[51] Int. Cl.$^3$ .................... G01N 33/48; G01N 33/54; G01N 21/07
[52] U.S. Cl. ......................................... 435/4; 422/64; 422/72; 422/101; 422/102; 436/45; 436/95; 436/514; 436/805; 436/810; 436/824; 435/14; 435/16; 435/21; 435/25; 435/28; 435/288; 435/291; 435/312; 435/808
[58] Field of Search ................ 23/230 B; 422/72, 73, 422/101, 102, 64, 67, 61; 366/340; 436/45, 95, 514, 805, 810; 435/4, 14, 16, 21, 25, 28, 288, 291, 312, 808

[56] References Cited

U.S. PATENT DOCUMENTS

| 3,532,470 | 10/1970 | Rochte ................................. 422/61 |
| 3,540,858 | 11/1970 | Rochte et al. ....................... 422/61 |
| 4,067,696 | 1/1978 | Curtis .................................... 422/47 |
| 4,103,876 | 8/1978 | Hasselman, Jr. et al. ... 261/DIG. 26 |
| 4,207,202 | 6/1980 | Cole, Jr. ............................. 422/133 |
| 4,225,558 | 9/1980 | Peterson et al. ..................... 422/72 |
| 4,237,234 | 12/1980 | Meunier ............................... 422/72 |
| 4,244,694 | 1/1981 | Farina et al. ..................... 422/72 X |
| 4,279,862 | 7/1981 | Bretaudiere et al. ................ 422/72 |
| 4,314,968 | 2/1982 | Guigan ............................. 422/72 X |

*Primary Examiner*—Michael S. Marcus
*Attorney, Agent, or Firm*—Felfe & Lynch

[57] ABSTRACT

The present invention provides a process for carrying out analytical determinations by mixing and incubating a sample solution with at least one reagent and optically measuring a parameter in the incubated reaction mixture. The mixing, incubating and measuring are carried out during the action of a centrifugal force which forces the solution through a plurality of interconnected small hollow spaces having flow resistance so adapted with regard to one another as to mix the reaction components. Incubation may also take place before the reaction solution passes from the plurality of interconnected small hollow spaces into a measuring chamber in which the measurement is carried out.

7 Claims, 12 Drawing Figures

METHOD FOR CARRYING OUT ANALYTICAL DETERMINATIONS

This invention relates to a method for carrying out analytical determinations. More specifically, the method involves the action of centrifugal force using the centrifugal analysis method.

With the increasing importance of clinical-chemical analysis, especially of blood and serum components, for medical diagnosis, processes and devices have been developed which reduce the analysis time and labour in order to handle the very considerably increased number of such analyses. An important step forwards was the development of automatic analysers. With the continuously increasing requirements of capacity, rapidity and variability of such automatic analysers, the cost for such apparatus has also increased to such an extent that the large modern automatic devices can only be used in especially high capacity clinics and institutes.

An important advance toward reducing the cost of such automatic analysers was provided by the principle of centrifugal analysis, described for the first time by Norman G. Anderson in Science, 166, 317–324/1969. This principle mixes the sample and reagent in a centrifugal rotor which, has a number of measuring chambers near its outer edge which permit the measurement of the reaction result while the rotor is still in movement, i.e. while the centrifugal force is still acting. It was thus possible to carry out a considerable number of identical investigations time. In the course of the further development of this analysis principle, the shape of the rotor, in particular, became increasingly complicated in order to improve the various working steps, such as mixing the reagents, incubation, reaction and the like. This led to the development of very complicated and laboriously constructed centrifugal analysis rotors which were not only increasingly expensive but, with increasingly complicated construction, were also larger. The advantages of the centrifugal analysis system, a simpler and thus also a cheaper manner of construction, were thus, in part, again sacrificed.

Therefore, there is still a need for a compact analysis system, the operation of which does not require highly qualified technical personnel. It should also operate quickly, give an analysis result which is independent of the operation of the apparatus and of the dexterity and attention of the operating personnel and allow all the required analyses to be carried out without changing the rotor.

SUMMARY OF THE INVENTION

It is an object of the present invention to provide such an analysis system, and which also permits completely different determinations to be carried out simultaneously in order, for example, to obtain profile analyses in a single working step.

Thus, according to the present invention, there is provided a process for carrying out analytical determinations by substantially dissolving at least one soluble dry reagent into and a sample liquid with the reagent for measuring a parameter in the reaction mixture, the mixing, dissolving, incubating, and measuring being carried out via the action of a centrifugal force. The centrifugal force brings the sample solution together with a soluble dry reagent, with at least partial dissolving thereof, and forces the mixture through a plurality of small hollow spaces. The centrifugal force and the flow resistance of the small hollow spaces are so adapted with regard to one another that a dissolving and mixing of the reaction components and possibly incubation takes place before the reaction solution passes from the small hollow spaces into a measuring chamber in which the measurement is carried out.

The process according to the present invention avoids the previously complicated construction of centrifugal analysis rotors. It is replaced by a quite simply constructed rotor which is adapted for the reception of exchangeable insert elements and which, in spite of its simple mechanical construction, makes all manipulations superfluous and merely requires the introduction of the sample solution.

The plurality of small hollow spaces provided according to the present invention acts counter to the liquid flow outwardly into the measuring chamber under the influence of the centrifugal force with such a flow resistance and, at the same time, brings about such a complete mixing of the sample solution and reagent in the sample solution that special mixing chambers, connecting channels and the like become superfluous. Solely by the selection of the dimensions of the small hollow spaces, every desired flow velocity and mixing intensity at a given centrifugal force can be achieved. The plurality of small hollow spaces can be achieved in a very simple way by using a mesh-shaped element such as an interwoven mesh, a paper strip, fleece or the like, or an open-celled foamed material, or a structured surface. The pores and depressions contained therein form the small interconnected hollow spaces, the use of which is an important feature of the present invention.

Therefore, the size of the hollow space corresponds to the size of the open spaces in such mesh-shaped elements and will normally not exceed about 2 mm., and preferably 1 mm., the lower limit being determined by the ability of the solution to pass through under the action of the centrifugal force.

The structured surface embodiment has a covering second surface which can be flat or also structured. The structured surface can be a roughened surface or one provided with a plurality of small pocket-like depressions. The connection between the individual very small hollow spaces is obtained by spacing the second surface a small distance from the first sufficient for the passage of liquids under the influence of gravity. If two structured surfaces are used, the structuring on each surface can be different so that, depending upon the speed of rotation of the rotor, differing effects can be brought about.

Elements with differing sizes of the small hollow spaces and correspondingly different flow resistances at a given centrifugal force can also be provided along the liquid flow path to the measuring chamber. In this way, it is possible, as desired, to increase or decrease the rate of flow in the individual sections of the flow path from the sample introduction point to the measuring chamber.

An important feature of the present invention is the possibility of providing several different dry reagents with which the sample solution is contacted under the influence of the centrifugal force. This allows the process according to the present invention to be used for multi-step analytical determinations in which different and successive reactions take place. It also makes it possible to separate different components of a reagent which are not compatible with one another, i.e. not only within the small hollow spaces but also outside of them.

According to a first embodiment of the process according to the present invention, the sample solution, which can be used more or less prediluted, is allowed to flow along a path provided with the very small hollow spaces in which the average hollow space size and the average flow resistance has the same value. This embodiment is especially useful for one-step processes. If desired, a path with increased flow resistance can follow as a braking path, for example in order to increase the incubation time before the reaction mixture enters the measuring chamber. This is explained in more detail hereinafter.

A further preferred embodiment of the process according to the present invention makes possible the use of two incubation steps and two different reagents. For this, the sample fluid is first allowed to flow through a first element having a plurality of very small interconnected hollow spaces which contains a first dry reagent. Downstream there is a second element with a plurality of very small interconnected hollow spaces with a greater flow resistance than the first element. This second element can be, for example, a mesh-shaped body with denser packing of the fibres than in the first element or can be a foamed material with comparatively small pores. Consequently, this second element has a greater flow resistance and brakes the fluid so that the first reaction can take place between the sample solution and the first reagent. Beyond this second element is then arranged a third element with a plurality of small interconnected hollow spaces which, in turn, possesses a lower flow resistance than the second element and which contains a second reagent different from the first one. Thus, in the case of this embodiment of the present invention, the sample solution flows through two incubation stages, between which is a braking path. If desired, a further braking path can be arranged to follow the third element.

A further preferred embodiment of the present invention corresponds to the above-described method with two incubation stages and a braking for the fluid therebetween but, between the second and the third element, an additional element is provided in which a separation can be carried out. In this additional, fourth element, the very small hollow spaces either have a reactive surface or are so constructed that they include a molecular sieve action.

In the case of a reactive surface, this either has groups acting as an ion exchanger or contains groups which manifest an affinity chromatography action or contains enzymatically or immunologically active bodies bound covalently or in some other manner. The fixing of substances of the above-mentioned kind, i.e. of substances which are enzymatically active or immunologically active or are suitable for affinity chromatography, on surfaces of solid bodies is well known and does not need to be described here in more detail. When the fourth element is, for example, a mesh-shaped body which consists of cellulose or polyamide fibres, then, for the activation of the surface, use can be made, for example, of the processes described in Federal Republic of Germany Patent Specifications Nos. 2,708,018 and 2,438,436. The same applies in the case of affinity chromatographically active substances which are fixed on to the fibre surfaces. In the case of surfaces with an ion exchange function, the fourth element can consist of one of the known ion exchange materials, for example can be based upon sulphonated or amidated polystyrene resins, cellulose fibres or cross-linked dextran gels. The fourth element with a chemically reactive surface can also consist of a dense packing of very small granules with reactive surfaces which can be made of substances known for this purpose. Examples of such materials include glass, metals, synthetic resins, ceramic granules and the like materials which are known to be useful as carriers for chromatographically or biologically active substances.

As mentioned above, the dry reagent is preferably arranged within the very small hollow spaces through which the sample fluid flows. However, it is also possible to place the reagent, for example in granulated or tabletted form, before the very small hollow spaces or in an interruption thereof. If, by appropriate choice of the centrifugal force and of the size of the small hollow spaces, the rate of flow is correspondingly small, the contact time between the solid reagent and the sample solution can be fixed within wide limits so that sufficient time is available for complete dissolving of the reagent into the sample solution. However, depending upon the nature of the reagent used, it may suffice when only a part thereof is dissolved. In these cases, the reagent is preferably used in an excess over the amount necessary for the reaction with the sample solution. The reagent can also contain sparingly soluble or insoluble particles which dissolve into the sample solution only slowly or not at all. Such insoluble particles should have a particle size substantially below the size of the small hollow spaces and their connecting openings in order to ensure a satisfactory passage through the small hollow spaces. However, it is also possible, on a part of the path, so to construct the very small hollow spaces that they exert a sieve function on such insoluble particles.

The described method of working with the arrangement of elution and mixing paths, braking and incubation paths and reactive surface paths can, of course, also be supplemented by repetition of these process sections, for example by combining the three above-described methods of working in any desired way.

The measurement of the reaction results can be carried out by the methods usual for this purpose, for example, optically with the determination of the reaction end point or by recordal of a kinetic reaction. Conductivity measurements can also be carried out.

For the method, an insert element for a centrifugal analysis rotor comprises at least one analysis reagent in dry form and a plurality of very small interconnected hollow spaces which connect a sample providing chamber to a measuring chamber.

The insert element makes carrying out of the process according to the present invention especially simple and permits decisive constructional simplification as compared to previously known centrifugal analysis rotors.

The insert element is used in a rotor unit of a centrifugal analyser. The rotor unit has a rotor base connected with a drive and a rotor head which, in operation, is connected to the rotor base. The rotor head includes a plurality of the insert elements. Each insert element has a chamber for the reception of a sample fluid and, radially outwardly from the sample chamber, a measuring chamber for the detection of components of the sample. Fluid channels connect the sample chambers and the measuring chambers. The rotor unit is characterised in that the rotor head includes a plurality of different insert elements which are connected exchangeably and at different positions with the rotor base. Such a rotor unit is described in more detail in our simultaneously filed German Patent Application entitled "Rotor unit with insert elements for a centrifugal analyser".

The fluid channel of the insert element can consist solely of a mesh-shaped element which defines a plurality of very small interconnected hollow spaces. Examples of such mesh-shaped elements include interwoven meshes, fleeces, papers, open-celled foamed materials, tightly packed small bodies and the like. When the insert element consists solely of such an element with very small interconnecting hollow spaces, then the analysis reagent is contained in the hollow spaces in dry form. In the simplest case, such an insert element can thus consist only of a piece of fleece or paper impregnated with the analysis reagent. Such an insert element can, for example, be employed in a rotor body which has a number of circularly arranged sample supply chambers connected by radial slots to a number of measuring chambers radially outwards therefrom. The insert element according to the present invention are tightly and fittingly inserted into these slots. The sample solution is introduced into the sample supply chamber and, after closure by a rotor cover plate or the like, a predetermined centrifugal force is produced, under the influence of which the sample fluid is spun outwardly through the fleece or paper insert element. The fluid hereby flows through the many very small interconnected hollow spaces, dissolves the dry reagent, mixes and incubates due to the deflection of the direction of flow in passing from one very small hollow space to the next, and finally passes into the measuring chamber in which a measurement is carried out in known manner.

However, in a further embodiment of the insert element the insert element can also have the sample reception chamber and/or measuring chamber, in addition to the element having the plurality of very small interconnecting hollow spaces. Such an embodiment of the insert element according to the present invention can, for example, consist of the element having the very small hollow spaces in the form of a longitudinal body wrapped in a synthetic resin foil, which, on at least one narrow end of the longitudinal body, forms a loop which defines a measuring chamber and/or a sample providing chamber. Such an insert element can, for example, be produced in an extremely simple manner by laying a paper or fleece strip impregnated with the dry analysis reagent on to a synthetic resin foil which projects slightly on both sides, for example by 0.5 to 1 mm. On one end, the foil is folded over and laid on the other side of the strip in such a manner that a small loop is formed with the folded over end. By sealing the projecting edges of the foil, the finished insert element is obtained. Instead of a foil, correspondingly shaped bodies of synthetic resin or similar shapable material can, of course, also be employed.

The insert element can contain several different analysis reagents spatially separated from one another. As already mentioned, the analysis reagents can be present within the very small hollow spaces. For example, a definite amount of a solution of the analysis reagent is applied to a point of the element having the small hollow spaces, such as a fleece or paper strip, and dried, for example, by lyophilisation or by some other method of drying. Alternatively, the analysis reagent can also be present in the insert element according to the present invention as a formed body, for example, in the form of a granulate, in tabletted form or the like but then in general is placed outside of the very small hollow spaces.

The insert element can be made reactive on at least a part of the surface of the small hollow spaces. As already mentioned above, the mesh-shaped body can then consist of fibres or filaments on the surface of which are fixed reactive substances, for example enzymatically or immunologically reactive substances. Reference is made to the above embodiment in the scope of the explanation of the process according to the present invention.

In the case of the insert element, several elements or bodies having the plurality of very small interconnected hollow spaces can be arranged side by side or, preferably, behind one another. This makes it possible, by means of different sizes of the small hollow spaces, to provide different flow resistances and thus also rates of flow, without varying the centrifugal force by changing the speed of rotation. In the case of a mesh-shaped element, the flow resistance is, for example, caused by the thickness of the fibres and the nature of their connection. With decreasing fibre diameter, the average diameter of the small hollow spaces becomes smaller and the flow resistance increases correspondingly. The nature of the connection of the individual fibres also influences the size of the openings between the very small hollow spaces and, by utilisation of this effect, the flow resistance can be adjusted to a definite desired value. In this way, it is possible, within the insert element, to provide paths with a greater and lesser flow resistance and thus to bring about an acceleration or braking of the rate of flow of the reaction solution.

A preferred insert element is characterised in that, between the sample supplying chamber and the measuring chamber, sections are arranged with differing average hollow space sizes which have differing flow resistances for a throughflowing fluid.

A further preferred insert element is characterised by a first element which has a plurality of very small interconnecting hollow spaces and contains a first reagent, a second element, arranged therebehind in the direction of flow, with a plurality of very small interconnecting hollow spaces with a greater flow resistance than the first element and a third element, arranged therebehind in the direction of flow, which has a plurality of very small interconnecting hollow spaces which possess a lower flow resistance than the hollow spaces of the second element and which contains a second reagent.

A further preferred insert element is characterised in that, between the second and third element, it has a further element with a plurality of very small interconnecting hollow spaces which have a reactive surface.

Such an insert element also contains elements which have enzymatically or immunologically active substances bound to the surface thereof.

A further preferred insert element contains elements, the surfaces of which have reactive groups with ion exchange properties.

The process according to the present inventin for the carrying out of analytical determinations and the rotor insert elements suitable therefor are described hereinafter in more detail, with reference to the accompanying drawings, in which.

Figure 1:
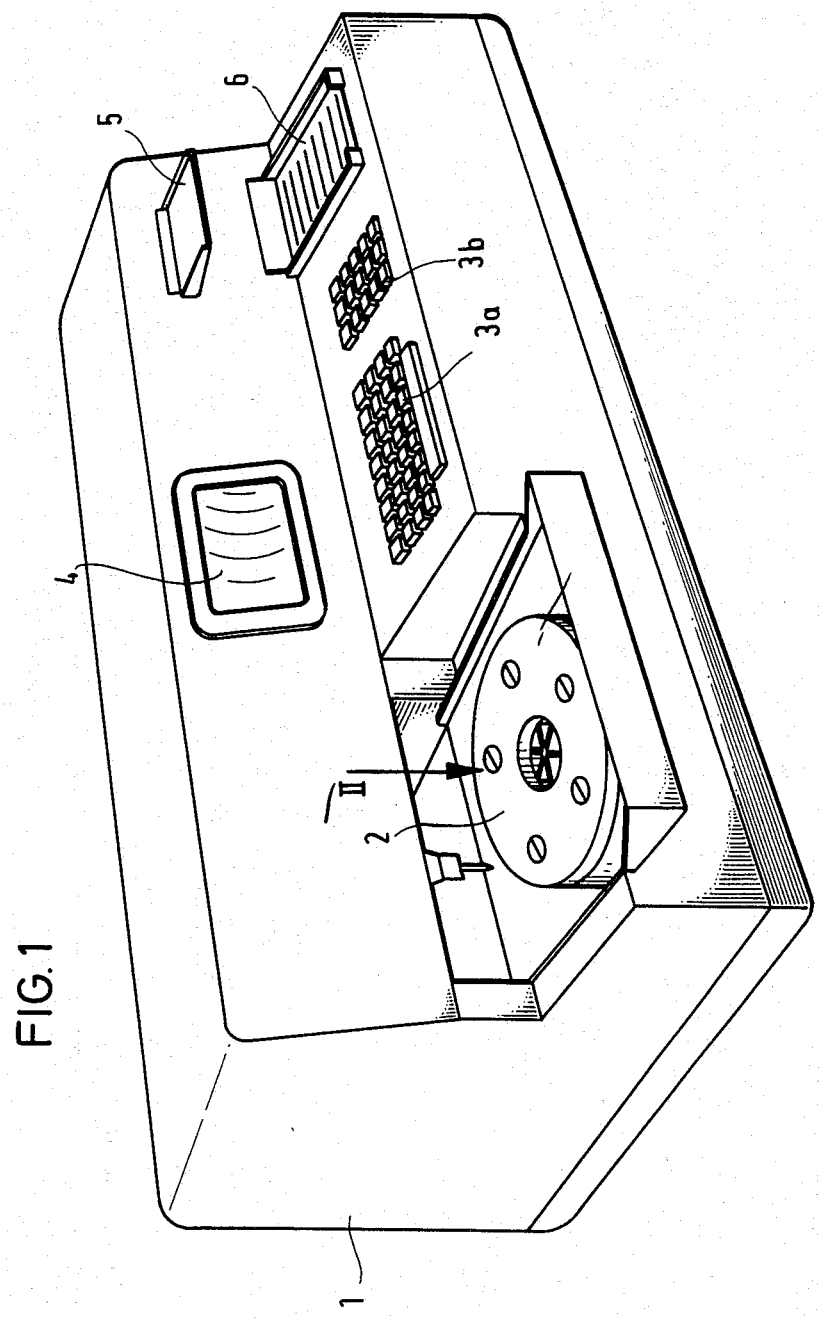
FIG. 1 is an external view of a centrifugal automatic analyser which is suitable for the use of the present invention.

FIG. 1 is an external view of a centrifugal analysis apparatus which is suitable for the present invention. A housing 1 accommodating the individual parts of the apparatus contains a centrifugal rotor 2. The illustrated embodiment of the rotor corresponds to the rotor illustrated in more detail in FIGS. 2 and 3. The rotor is fixed to and driven by a driving element (not illustrated) in the usual manner for such analysis apparatus or centrifuges. Two banks of operating buttons 3a and 3b enable the necessary manipulations and engagements in the control to be carried out. A screen 4 makes possible the optical reproduction of analysis results and the calling up of fed-in information. 5 and 6 are insert and removal stations for magnetic cards, holerith cards or like storage devices for information to be fed into the apparatus.

Figure 2:
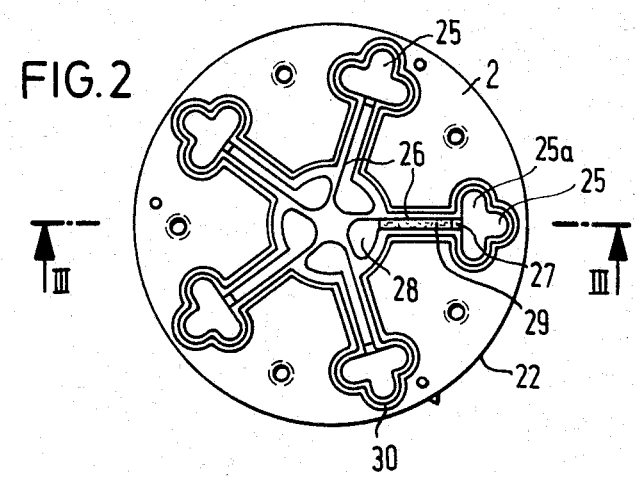
FIG. 2 is a section through the plane of a centrifugal analyser rotor.
Figure 3:
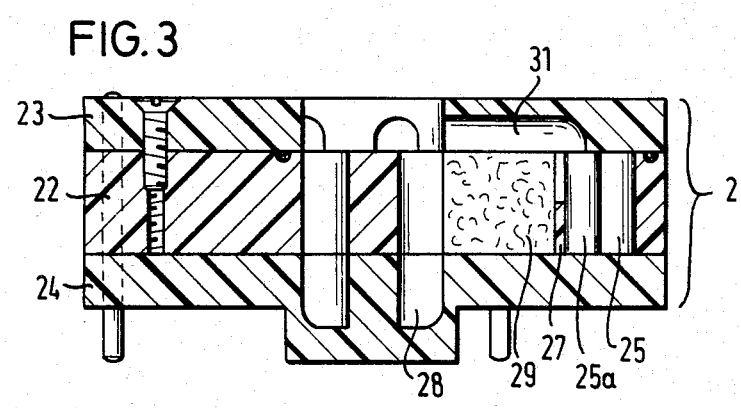
FIG. 3 is a vertical section through the rotor of FIG. 2.

FIGS. 2 and 3 illustrate a rotor construction suitable for the present invention which, in principle, comprises three round discs fixed on one another, FIG. 2 being a view of the middle disc and FIG. 3 a section through the rotor on the line III—III.

The rotor 21 consists of a middle disc 22 and two transparent synthetic resin plates 23 and 24, which serve as base and cover. In the middle disc 22, for example coloured black, of, for example, 6 mm. height and 33 mm. diameter, on a radius of, for example, 14 mm., are arranged five equally distributed holes 25 of, for example, 1.7 mm. diameter which serve as measuring chambers and especially as cuvettes. Towards the middle point of the disc 22, each measuring chamber 25 is connected to an antechamber 25a of, for example, 2 mm. $\times$ 5 mm. Thereafter follows a slit-like channel 26 of, for example 6 mm. length and 1 mm. width. The channel 26 is, up to half its height, separated from the antechamber by a barrier 27 which prevents a flowing back of the solution during the mixing step. Before the channel 26, towards the inside, there is a sample chamber 28 with a diameter of, for example, 3 mm. It continues downwardly as a depression the base part 24 and is so constructed that the forces occurring during acceleration of the rotor drive the diluted sample into the elution channel 26. The depression in the base part 24 is, for example, so dimensioned that 20 $\mu$l. do not quite fill up to the elution channel. The volume needed for filling the cuvette 25, including the losses due to retention on the insert element 29, is, for example, 18 $\mu$l. The insert element 29 consists of a rectangular paper strip impregnated with an analysis reagent in solid form which is inserted with a tight fit into the slit-like channel 26.

The base part 24 and the cover part 23 consist, for example, of a transparent plastics material and also form the windows for the cuvettes 25. The bottom 24 is, for example, connected by ultrasonic welding to the middle part 22. The cover 23 is only screwed on and silicone rubber seals 30 can be arranged around cuvettes 25 and channels 26. In the cover 23 and over the channels 26 there are provided recesses 31 which prevent fluid being sucked back by the capillary action of the slot between the middle body 22 and the cover part 23.

Figure 4:
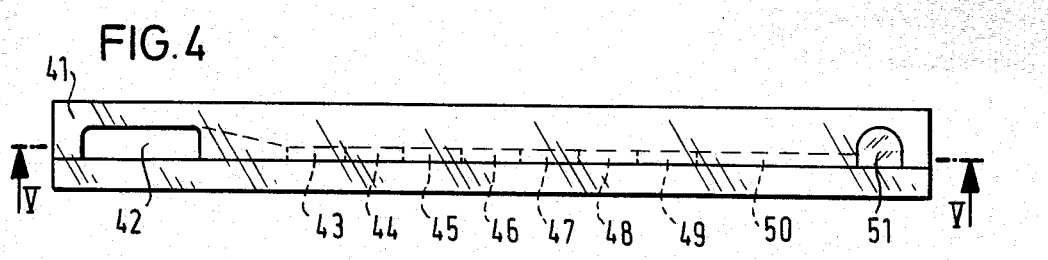
FIG. 4 is a side view of an insert element.
Figure 5:
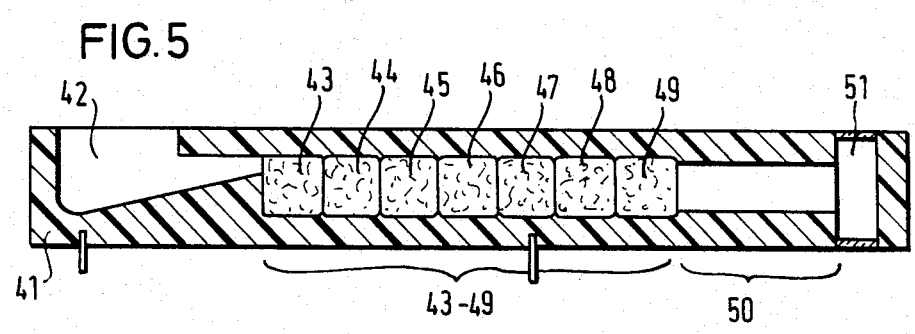
FIG. 5 is a longitudinal section through the insert element of FIG. 4.
Figure 7A:
FIGS. 7a, 7b and 7c are schematic illustrations of structured surfaces with very small interconnecting hollow spaces.
Figure 7B:
Figure 7C:
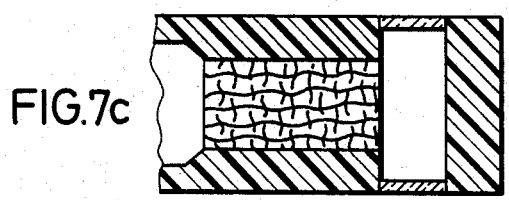

FIGS. 4 and 5 show a further insert element. according to the present invention which is constructed as a disposable part and is suitable for use on a comparatively large rotor. The insert element 41 comprises, from left to right, a sample chamber 42 and a number of zones 43, 44, 45, 46, 47, 48 and 49 into which insert bodies with a plurality of interconnecting hollow spaces can be inserted which, for example contain reagents, can brake the fluid current, can have a reactive surface, etc. The zones 43 to 49 are followed by a path 50 constructed as a mixing zone and a measuring chamber (cuvette) 51. The path 50 can consist of two structured surfaces lying closely together or of a mesh, as is described in more detail for FIGS. 7a to 7c. If the zones 43 to 49 are filled, for example, with paper strips or fleece as insert bodies or elements with a plurality of very small interconnecting hollow spaces, then these can be constructed corresponding to the process steps described above in detail. If, for example, glucose is to be determined with the insert element 41, then zone 43 contains a fleece impregnated with a buffer substance, zone 44 a fleece impregnated with 4-aminoantipyrine and zone 45 a fleece impregnated with the necessary enzymes and the phenol components, these chemical substances being, of course, present in dry form.

In operation, into the sample supply chamber 42 there is introduced the sample diluted with water or some other appropriate aqueous solution, the minimum amount of which is determined by the cuvette volume and the amount of solution remaining behind on the fleece for the radius of the rotor and the speed of rotation. After commencement of the rotation, the diluted sample flows through the fleeces in zones 43 to 49, whereby in zones 46 to 49 there can be provided further reagents and/or active surfaces and/or means for changing the speed of flow. The sample successively dissolves the necessary amounts of buffer, 4-aminoantipyrine, enzymes and phenol, whereby the reaction is also started. In zones 46 to 49 and in the mixing path 50 or possibly solely in the mixing path 50, there is achieved a good mixing up of the solution. Then the already reacting solution flows into the cuvette 51 where the reaction can be measured in the manner known for centrifugal analysers.

The insert element 41 according to the present invention permits, in zones 46 to 49, the incorporation of elements with a plurality of very small interconnecting hollow spaces which are effective as braking bodies, separating columns, etc. Braking bodies are, for example, elements with very small pores which pass the fluid, for example, only after 5 or more minutes so that in these zones a pre-incubation also takes place. Zones with elements which have chemically reactive surfaces can be used as separating columns. The same applies to inserts which are effective as molecular sieves.

The use of insert elements for zones 46 to 49 which serve as braking chambers or separating columns explained in more detail in the following example of the determination of thyroxine ($T_4$). The zones illustrated in FIGS. 4 and 5 then have inserts, for example of paper fleece, which are impregnated with the following substances or display the following effectiveness:

43 first buffer and detergent
44 marked antigen ($T_4$-POD) (POD = peroxidase)
45 $T_4$-antibody (AB)
46 braking chamber (incubation path)

47 separating column (antibody against anti-T4)
48 second buffer, glucose oxidase
49 colour-developing substrate (e.g. phenol and 4-aminoantipyrine)

$T4_p$ = T4 from the sample

The reactions thereby proceed according to the following scheme:

$$T4_p + T4\text{-POD} + AB \rightarrow T4_p{}^*AB + T4\text{-POD-}{}^*AB + T4_p + T4\text{-POD}$$

in which * indicates the antigen-antibody complex.

This reaction takes place in the incubation path 46. The separating column 47 contains bound antibody against anti-T4 so that it completely absorbs $T4_p{}^*AB$ and T4-POD*AB. $T4_p$ and T4-POD pass through the column 47. After the solution freed from the antibody complexes has passed the sections 48 and 49 and has dissolved the reagents present therein, the solution enriched in this way passes into the cuvette 51 in which the POD activity of the T4-POD forms a coloured complex from phenol+4-aminoantipyrine by means of the hydrogen peroxide produced from the sample glucose under the influence of GOD, the concentration increase of the coloured complex being measured at 500 nm.

Figure 6:
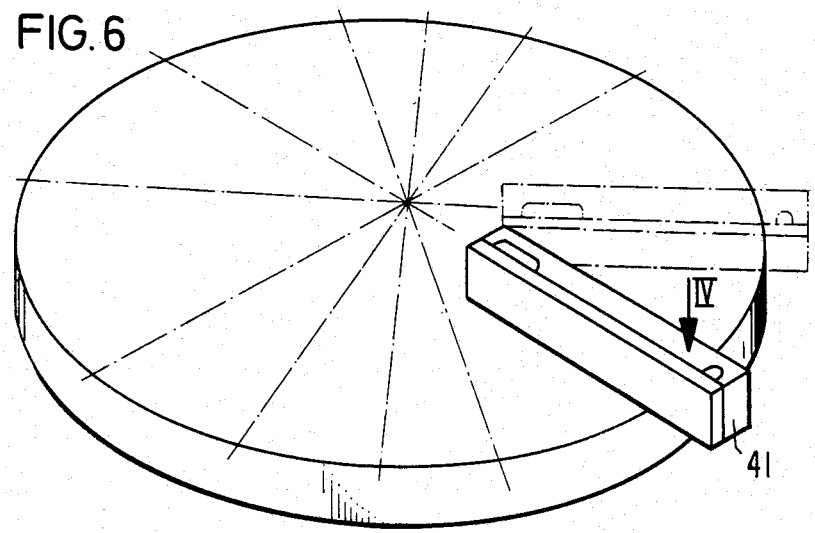
FIG. 6 is a schematic view of the insert element of FIGS. 4 and 5 on a rotor.

As can be seen from FIG. 6, 41 insert element is so fixed on to a rotor, by holding means here not shown, that a sample can be introduced from above by means of an appropriate dosing device and a transillumination of the cuvette for the measurement of the reaction result can also be carried out.

FIG. 7 shows schematically possible arrangements of the very small hollow spaces, a and b illustrating structured surfaces and c a mesh-shaped element.

The insert elements according to the present invention can also be bundled together to give larger segment-shaped units. This allows an analysis profile to be determined in a single working step since each individual element permits the determination of another parameter of the introduced sample. Such segment-shaped insert element bundles can also be used for the simultaneous measurement of a particular parameter in a plurality of samples. In this case, each insert element in the insert element bundle contains its own sample introduction chamber. It is clear that any desired combinations between these embodiments are possible so that many identical and/or different determinations can be carried out simultaneously. The insert elements can be made to be reusable but are preferably disposable.

The reagents can be present in mixed form or as individual components which, when the sample fluid flows through, are successively dissolved and mixed with one another. In this case, the various meshshaped elements arranged in the insert element can consist of individual paper strips each of which contains a definite amount of reagent impregnated therein. Such individual components of a carrier containing an analysis reagent are described, for example, in Federal Republic of Germany Patent Specification No. 2,852,994.

With the process and insert element according to the present invention, there can, in principle, be carried out all known determinations of blood and serum components, as well as other analytical determinations. The following Table 1 gives a number of examples of methods of determination which require a single incubation step and can be carried out according to the present invention (Type 1). The Table gives the parameter to be determined, the preferable dilution of the sample, the period of time of the determination in seconds, the measurement technique to be used and the number of reagent segments needed.

TABLE 1

| parameter | dilution factor | measurement time (total) | measurement technique | reagent segments |
|---|---|---|---|---|
| glucose | 100–200 | <100 s | pseudo-EP | 3 |
| total bilirubin | 10 | 60 s | EP; polychrom. | 1 |
| creatinine | 10 | <90 s | pseudo-EP | 2 |
| albumin | 200 | 30 s | EP; polychrom. | 1 |
| total protein | 50 | <90 s | pseudo-EP | 1(2) |
| iron | 4 | 90 s | EP; polychrom. | 3 |
| haemoglobin | 250 | 165 s | EP; polychrom. | 2 |
| urea | 100 | 60 s | pseudo-EP | 3 |
| uric acid | 50 | 120 s | pseudo-EP | 3 |
| triglycerides | 50 | 150 s | pseudo-EP | 3 |
| cholesterol | 100–200 | 150 s | pseudo-EP | 3 |
| chloride | 50 | <60 s | EP; polychrom. | 1 |
| calcium | 50 | <60 s | EP; polychrom. | 2 |
| phosphate | 50 | 100 s | pseudo-EP | 2 |
| γ-GT | 10 | 90 s | kinetic | 2 |
| AP | 50 | 120 s | kinetic | 3(4) |
| GOT | 10 | 90 s | kinetic | 3 |
| GPT | 10 | 90 s | kinetic | 3 |
| LDH | 100 | 60 s | kinetic | 2 |

EP = end point determination
pseudo-EP = process in which, with the help of a known mathematical process, initial and end extinctions are calculated.

In an analogous manner, there can also be determined, for example, lactate, ammonia, lipase, amylase and creatine kinase.

The following Table 2 gives further parameters which can be determined according to the present invention and which require more than one incubation step and make possible, for example, the determination of a thyroid profile, the determination of specific proteins, the determination of coagulation parameters and the determination of active materials.

TABLE 2

| parameter | dilution factor | measurement time | measurement technique | reaction/ reagent segments |
|---|---|---|---|---|
| lipase | 25 | 180 s | kinetic | 2 |
| amylase | 100 | 180 s | kinetic | 2 |
| creatine kinase | 10 | 180 s | kinetic | 3 |
| thyroid profile: | | | | |
| T4 | | | analogue T4[1] | 7 |
| triiodothyronine | | | analogue T4 | 7 |
| thyroxine-binding globulin | | | " | 7 |
| thyreotropin | | | " | 7 |
| enzymes: | | | | |
| acid phosphatase | | | analogue T4 | |
| coagulation: | | | | |
| opt. quick | | 360 s | kinetic | 3 |
| heparin | | 360 s | " | 3 |
| plasminogen | | | " | 3 |
| antiplasmin | | | " | 3 |
| prothrombin | | | " | 3 |
| antitrypsin | | | " | 3 |
| drugs: | | | | |
| digoxin | | | analogue T4 | 7 |
| digitoxin | | | " | 7 |
| phenytoin | | | " | 7 |
| phenobarbital | | | " | 7 |
| primidone | | | " | 7 |
| carbamazepine | | | " | 7 |
| gentamycin | | | " | 7 |
| tobramycin | | | " | 7 |
| amykacin | | | " | 7 |
| opiates | | | " | 7 |
| barbiturates | | | " | 7 |
| methadone | | | " | 7 |
| amphetamine | | | " | 7 |

TABLE 2-continued

| parameter | dilution factor | measurement time | measurement technique | reaction/reagent segments |
|---|---|---|---|---|
| cocaine | | | " | 7 |
| morphine | | | " | 7 |
| benzodiazepine | | | " | 7 |
| propoxyphene | | | " | 7 |
| theophylline | | | " | 7 |
| methotrexate | | | " | 7 |
| cancer indicators: | | | | |
| $\alpha_1$-foetoprotein | | | analogue T4 | 7 |
| carcinoembryonal antigen | | | " | 7 |

[1]see the preceding description of the measurement of T4.

The present invention also makes it possible to determine specific proteins, such as IgG, IgA, IgM, transferin, $\alpha_1$-AT, $\alpha_2$-macroglobulin, haptoglobulin, $\beta$-lipoprotein, $\alpha_1$-glycoprotein and albumin, the TINIA measurement technique being employed and the dilution factor preferably being 1:100, the increase of the turbidity in a solution by the formation of the hapten-antibody complex thereby being measured. The process is well known. For these determinations, one incubation step suffices and, consequently, the provision of two reagent segments.

The above statements show that the present invention provides an analysis system which combines the following advantages: only a minimum of manipulations is necessary from taking the sample to obtaining the final analysis result; not only a plurality of simple, frequently required analyses but also special, complicated individual analyses can be carried out in the same manner; the amount of sample volume required is reduced to a minimum, with corresponding minimisation of the reagent requirement and reagent costs; the carrying out can take place simply and with personnel who are not highly trained; and the analysis frequency is as high as in the case of the most rapid known automated analysis systems.

According to the present invention, it is surprisingly, also possible to dissolve the solid reagent in substantially smaller amounts of sample fluid and thus to obtain more concentrated solutions than is possible under otherwise comparable conditions without the influence of centrifugal force.

Furthermore, the present invention permits the use of various measurement methods, such as optical transillumination, nephelometry, turbidimetry, reflection measurement, fluorescence measurement, luminescence measurement, radioactive radiation measurement and electrical measurements, such as conductivity and the like.

The following Examples are given for the purpose of illustrating the present invention:

EXAMPLE 1

This Example describes the carrying out of the present invention with the use of a rotor such as is illustrated in FIGS. 2 and 3 of the accompanying drawings.

(a) Measurement procedure

Insert element

A fibre fleece is used which contains 40% polyamide fibres and 40% regenerated cellulose. It has a take-up capacity for aqueous solutions of about 500 ml./m² in the case of a thickness of 0.5 mm. and a weight per unit surface area of 75 g./m² (VS 532 of the firm Binzer). For loading, impregnation solutions of reagents of appropriate concentration are prepared. These are either applied dropwise with a pipette or applied in an impregnation plant, the paper thereby being dipped into the impregnation solution, whereafter excess solution is squeezed off between two rollers and the paper dried in a current of air. The amounts necessary for the loading are given from the concentration required in the cuvette and the different degrees of elution for the reagents.

The cut up reagent papers (2 mm.×6 mm. to 6 mm.×6 mm.) are inserted into the slits 26 of the rotor (FIG. 2). Because of the shortness of the channel, the breadth amounts to 1 mm. and at least two fleeces are positioned next to one another in order to prevent a slipping of the fleece. The fleeces are inserted with the help of tweezers and the removable cover, which is also the cuvette window, is again screwed on. 18 μl. of diluted sample solution are introduced into the sample chamber. Centrifuging at 2880 r.p.m for 1 second to 25 seconds, the diluted sample is transported into the first fleece and dissolves the reagent.

Centrifuging at 12000 r.p.m. for 5 seconds, the solution is driven from the fleece into the cuvette, only minimal amounts of solution remaining behind on the fleece. Mixing is subsequently carried out.

The mixing procedure consists of 1 second acceleration to 12000 r.p.m. and 1 second stop and is repeated 6 to 20 times. By means of the acceleration and braking steps, the solution is mixed in the cuvette antechamber. This shaking cycle is not necessary when, after the last fleece, a comparatively long path is available on which mixing bodies are arranged. Subsequently centrifuging is carried out for 4 seconds at 12000 r.p.m. in order to drive out air bubbles and sediment, for example fibres from the light path before the measuring speed is switched on. Measurement takes place at 2830 r.p.m.

This embodiment is especially suitable for the determinations set out above in Table 1.

(b) Determination of glucose

Test composition
100 mM sodium phosphate buffer, pH 7.0
0.77 mM 4-aminoantipyrine
11 mM phenol
>18 U/ml. glucose oxidase
>1.1 U/ml. peroxidase
Loading of the paper (impregnated)
Enzyme/dyestuff fleece, 6 mm.×6 mm., is impregnated with a solution containing
  1630 mU glucose oxidase
  210 mU peroxidase
  8.4 μg. aminoantipyrine
and dried.
Buffer fleece, 3 mm.×6 mm., is impregnated with a solution containing
  228 μg. disodium hydrogen phosphate
  312 μg. sodium dihydrogen phosphate
and dried.
The coupler, phenol, was added to the diluted sample in a concentration of 11 mM.
Measurement conditions:
  dilution 1:100 with 0.2% Triton-X-405+11 mM phenole in dist. H₂O
  first centrifuging at 2880 r.p.m. for 5 seconds
  6 times mixing
  fleece arrangement:
    ½ enzyme/dyestuff
    buffer ½ enzyme/dyestuff
Measurement of the absorption at 500 nm Evaluation takes place according to the pseudoend point method, i.e. by adaptation of the measurement points of 25 to 70 seconds to the function according to a known mathematical method.

Measurement results:
Linearity

Figure 8:
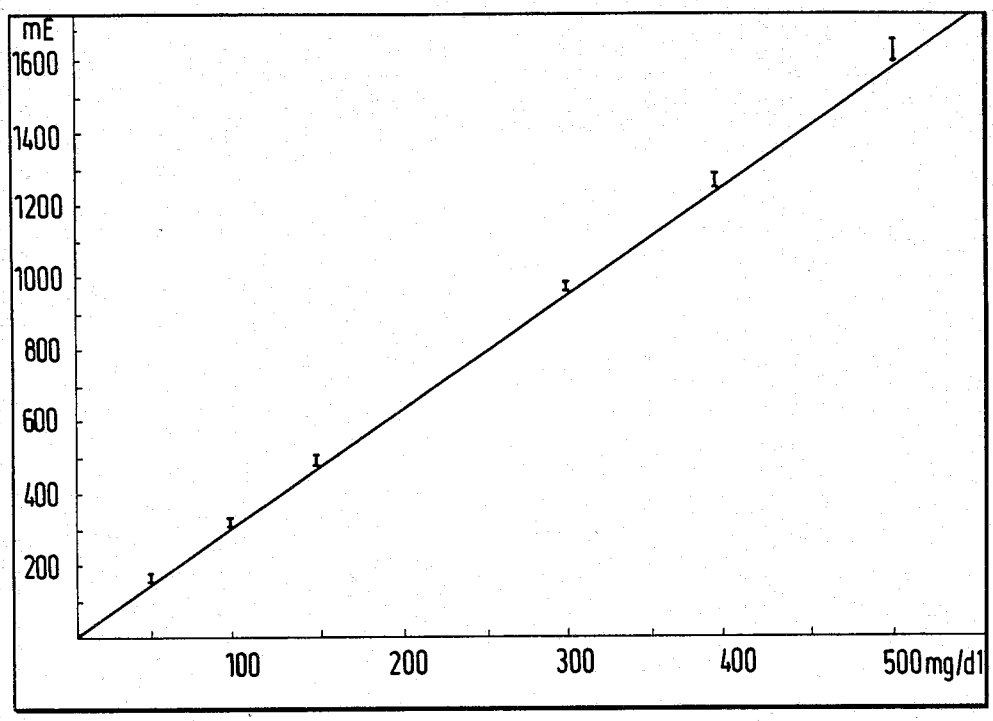
FIGS. 8, 9 and 10 are graphic illustrations of the analysis results obtained according to the Examples given hereinafter.
Figure 9:
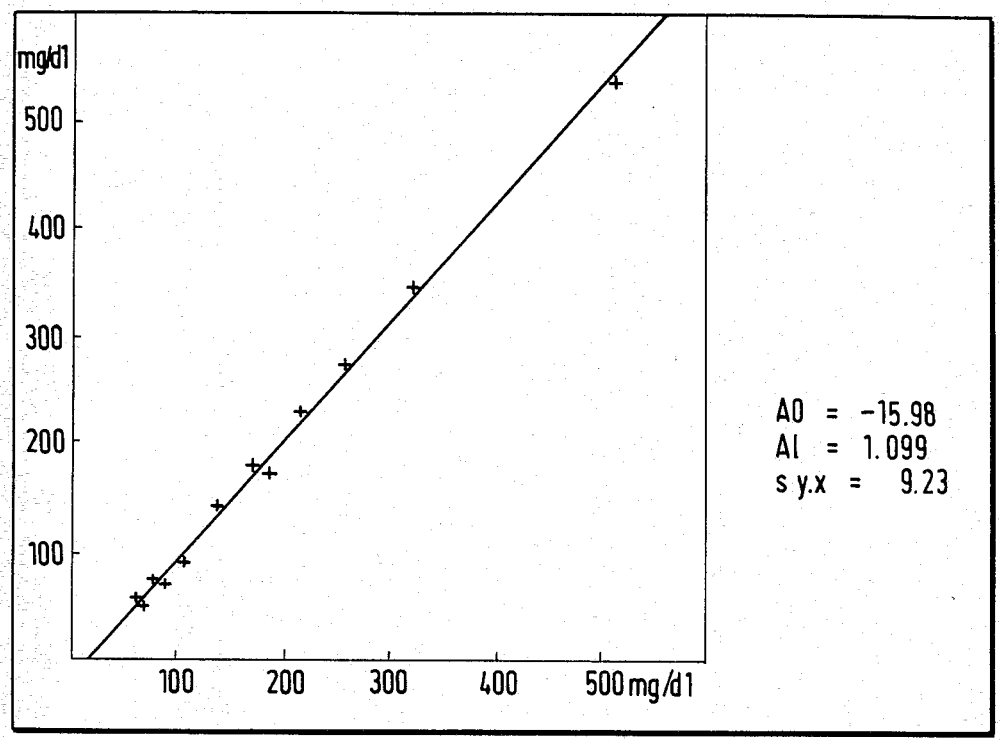

Aqueous glucose standards were measured with the use of a rotation photometer. The results are illustrated graphically in FIG. 8. For the purpose of method comparison, values determined according to the present invention were compared with manually determined values. In both cases, calibration was with the standard 100 mg./dl. The results are shown in FIG. 9 which, in graphic representation, gives on the abscissa the manually determined values and on the ordinate the values determined according to the present invention.

Example 2

Determination of GOT (aspartate aminotransferase)

The procedure was as described in Example 1, with the use of an insert element according to FIGS. 2 and 3 of the accompanying drawings.

1. Test composition.

The required concentrations were selected analogously to various recommendations
   80 mM tris, pH 7.8 at 30° C.
   240 mM L-aspartic acid
   12 mM α-ketoglutaric acid
   2000 U/l. malate dehydrogenase (MDH)
   3000 U/l. lactate dehydrogenase (LDH)
   0.23 mM NADH As reference test, there was employed the monotest GOT according to IFCC, order No. 300667, Boehringer Mannheim.

2. Loading of the papers (impregnated)
   buffer fleece, 3 mm.×6 mm., containing
   407 μg. tris base
   1340 μg. aspartic acid
   pH 7.8 with NaOH at 30° C.
   Enzyme fleece, 3 mm.×6 mm., containing
   84 mU MDH
   126 mU LDH
   76 μg. sodium ketoglutarate
   pH of the impregnation solution was 7.4.
   Dyestuff fleece, 3 mm.×6 mm., containing
   6 μg. sodium NADH
   pH 9.95 with 11 mM sodium carbonate 3. Measurement conditions
   Dilution 1+10 with 0.02% Triton-X-405
   First centrifuging at 2880 r.p.m. for 1 second 6 times mixing.
   Fleece arrangement:
   ⅔ enzyme
   buffer
   ⅔ dyestuff
   Measurement of the absorption at 340 nm.

4. Measurement results
   Precision and linearity

Figure 10:
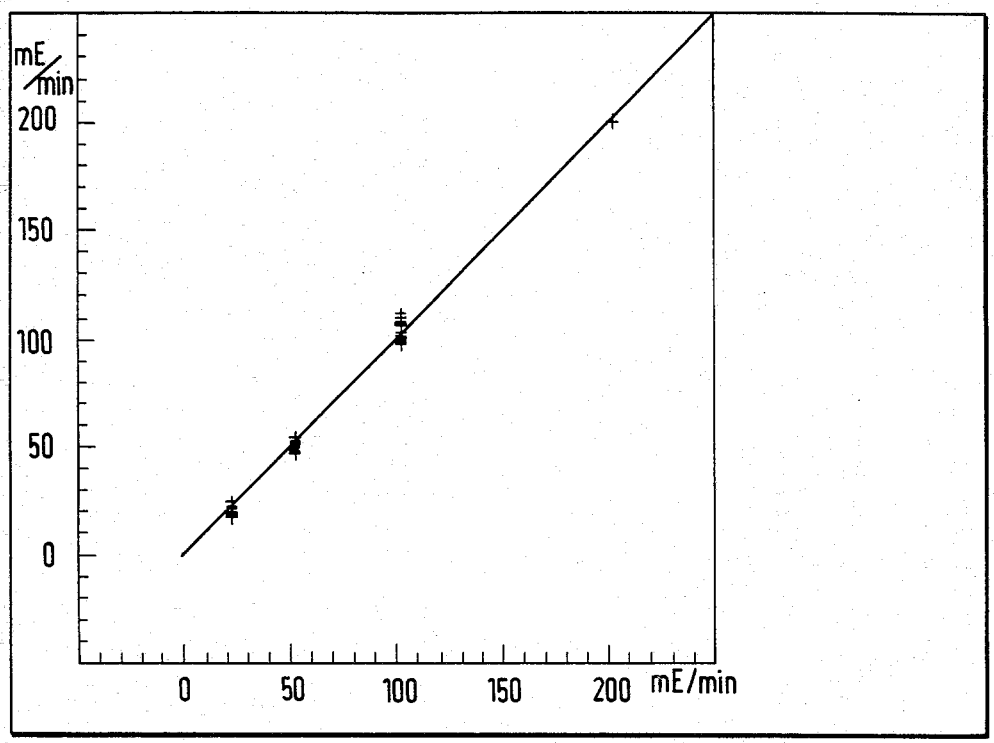

Measurement was carried out on a rotation photometer with 13 different dilutions of the control serum (Percipath E of Boehringer Mannheim). In each case, four concentrations were measured in one rotor, one of which serves as a calibration value. FIG. 10 shows the results obtained.

EXAMPLE 3

Alkaline phosphatase

The determination took place as in Example 2 with the following test composition:

The manual test as reference method is carried out with the here-given concentrations.
   0.6M D(−)-N-methylglucamine
   4 mM magnesium L-aspartate
   12 mM di-tris-(p-nitrophenyl)phosphate
   7.7 mM tris (trishydroxymethylaminomethane)
   0.2% Triton-X-405
   pH 10.45 (adjusted at 25° C. with hydrochloric acid)
   Loading of the paper (dropped on and dried):
   substrate fleece, 3 mm.×6 mm.
   130 μg. tris pNPP
   12 μg. tris
was dried in a vacuum over silica gel.
   Buffer fleece A, 4 mm.×6 mm.
   2362 μg. methylglucamine
   232 μg. methylglucamine hydrochloride
   58 μg. magnesium aspartate
   Buffer fleece B, 4 mm.×6 mm.
   3836 μg. methylglucamine
   Measurement conditions:
   Dilution 1+40 with 0.2% Triton
   First centrifuging at 2880 r.p.m. for 25 s 20 times mixing

| Fleece arrangement: | buffer A (centre) buffer B | adjuvant fleece (cuvette) substrate |
|---|---|---|
| Measurement of the absorption at 410 nm. Measurement results: Precision: | | |
| Normal range, 60 to 170 U/l. (opt.) | | sample 100 U/l. n = 13 A = 33.2 mE/min. CV = 8.7% |
| Pathological range, >170 U/l.: | | sample 500 U/l. n = 16 A = 145.4 mE/min. CV = 4.4% |

EXAMPLE 4

Determination of Immunoglobulin G using an insert element according to FIGS. 4 and 5

Two filtre fleeces (as described in example 1) of the size 6 mm×6 mm are impregnated with a solution of the following composition:
   50 mM phosphate buffer, pH 7.5
   25 g/l PEG 6000
   Anti-IgG from sheep (Mancini-titer 15–30).

The reaction takes place according to the following principle: IgG+Anti-IgG→IgG+Anti-IgG-complex. The complex causes an increase in the turbidity of the solution, the optical density of which can then be measured and used for the determination of IgG concentration according to a known procedure.

Calibration is carried out using 3 standards of known concentration.

Execution of the determination

The paper fleeces described above are inserted into position 43 and 44 of a plastic element of the type according to FIGS. 4 and 5. The plastic element is sealed with a plastic foil.

Human serum samples of unknown concentration are diluted 1:25 with 0.9% NaCl solution. 60 μl of the diluted sample are given into the application chamber 42.

The insert element is placed on the rotor of a centrifugal photometer. The initial speed of rotation is 200 r.p.m. After 15 seconds the speed of rotation is raised to 1500 r.p.m., driving the solution into the cuvette and at the same time freeing it of air bubbles. The photometric measurement takes place at 360 r.p.m. using 340 nm. The reading of the endpoint is carried out after 150 sec. Comparing the results with measurements carried out according to a known procedure, agreement is obtained with a correlation coefficient of 0.96 and a linearity range of 2500 mg IgG/100 ml sample.

It will be understood that the specification and examples are illustrative but not limitative of the present invention and that other embodiments within the spirit and scope of the invention will suggest themselves to those skilled in the art.

What is claimed is:

1. A method of carrying out an analytical determination on a liquid sample, comprising:
    (a) predisposing at least one dry reagent which is soluble in the liquid sample in at least some of a plurality of interconnected small hollow spaces;
    (b) centrifugally forcing the liquid sample into and through the plurality of interconnected small hollow spaces;
    (c) selecting the centrifugal force and the flow resistance of the plurality of interconnected small hollow spaces with regard to one another and so centrifuging for a period of time sufficient to allow the dry reagent to dissolve substantially in the liquid sample and to mix as reaction components in the plurality of interconnected small hollow spaces before they pass therefrom;
    (d) centrifugally passing the reaction components from the plurality of interconnected small hollow spaces to a measuring chamber; and
    (e) measuring a parameter of the reaction components in the measuring chamber to form the analytical determination.

2. A method as claimed in claim 1, wherein the step of centrifugally forcing the liquid sample into the plurality of interconnected small hollow spaces additionally comprises allowing capillary interaction of the liquid sample and plurality of interconnected small hollow spaces to draw the sample therein.

3. A method as claimed in claim 1 or 2, wherein the step of predisposing at least one dry reagent which is soluble in the liquid sample in at least some of the plurality of interconnected small hollow spaces comprises predisposing different reagents successively along the plurality of interconnected small hollow sapces in the direction the reaction components are forced therethrough.

4. A method as claimed in claim 1 or 5, wherein the step of predisposing at least one dry reagent which is soluble in the liquid sample in at least some the plurality of interconnected small hollow spaces comprises providing an additional reactive surface to at least some of the plurality of interconnected small hollow spaces, the additional reactive surface having ion exchange, affinity chromatography, enzymatic or immunological activity.

5. A method as claimed in claim 1 or 2, wherein the step of selecting the centrifugal force ad the flow resistance of the plurality of interconnected small hollow spaces comprises providing differing average diameters to successive portions of the plurality of interconnected small hollow spaces whereby the flow rate therethrough is varied.

6. A method as claim 1 or 2, wherein the step of selecting the centrifugal force and the flow resistance of the plurality of interconnected small hollow spaces further comprises selecting the same so as to provide an incubation time before the reaction components are passed to the measuring chamber.

7. A method as claimed in claim 1 or 2, wherein the step of predisposing at least one dry reagent which is soluble in the liquid sample in at least some the plurality of interconnected small hollow spaces comprises providing an additional reactive surface to at least some of the plurality of interconnected small hollow spaces, the additional reactive surface having chemically reactive activity.

* * * * *

UNITED STATES PATENT AND TRADEMARK OFFICE
CERTIFICATE OF CORRECTION

PATENT NO. : 4,515,889
DATED : May 7, 1985
INVENTOR(S) : Sigmar Klose et al.

It is certified that error appears in the above-identified patent and that said Letters Patent is hereby corrected as shown below:

Column 2, lines 20 to 21, delete "in the sample solution".

Claim 4, line 1, "5" should be -- 2 --.

Claim 5, line 2, "ad" should be -- and --.

Signed and Sealed this

First Day of July 1986

[SEAL]

Attest:

DONALD J. QUIGG

Attesting Officer

Commissioner of Patents and Trademarks